(12) United States Patent
Buschmann et al.

(10) Patent No.: US 8,877,753 B2
(45) Date of Patent: Nov. 4, 2014

(54) 1-ARYL-3-AMINOALKOXY PYRAZOLES AS SIGMA LIGANDS ENHANCING ANALGESIC EFFECT OF OPIOIDS AND ATTENUATING THE DEPENDENCY THEREOF

(75) Inventors: Helmut Heinrich Buschmann, Aachen (DE); Jose Miguel Vela Hernandez, Barcelona (ES); Daniel Zamanillo-Castanedo, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 629 days.

(21) Appl. No.: 12/988,951

(22) PCT Filed: Apr. 24, 2009

(86) PCT No.: PCT/EP2009/054974
§ 371 (c)(1),
(2), (4) Date: Dec. 17, 2010

(87) PCT Pub. No.: WO2009/130310
PCT Pub. Date: Oct. 29, 2009

(65) Prior Publication Data
US 2011/0112095 A1    May 12, 2011

(30) Foreign Application Priority Data
Apr. 25, 2008 (EP) .................................. 08380122

(51) Int. Cl.
| | | |
|---|---|---|
| *A61K 31/4152* | (2006.01) | |
| *A61K 31/4155* | (2006.01) | |
| *A61K 31/485* | (2006.01) | |
| *A61K 31/5377* | (2006.01) | |
| *A61P 25/36* | (2006.01) | |
| *C07D 231/22* | (2006.01) | |
| *C07D 401/12* | (2006.01) | |
| *C07D 403/12* | (2006.01) | |
| *C07D 471/04* | (2006.01) | |
| *A61K 45/06* | (2006.01) | |

(52) U.S. Cl.
CPC .......... *C07D 231/22* (2013.01); *A61K 31/4152* (2013.01); *C07D 471/04* (2013.01); *C07D 403/12* (2013.01); *C07D 401/12* (2013.01); *A61K 31/485* (2013.01); *A61K 45/06* (2013.01); *A61K 31/4155* (2013.01)
USPC .................. 514/236.5; 514/231.5; 514/239.2; 514/282; 544/106; 544/111; 544/140; 546/44

(58) Field of Classification Search
USPC ......... 514/236.5, 282, 231.5, 239.2; 544/106, 544/111, 140; 546/44
See application file for complete search history.

(56) References Cited

FOREIGN PATENT DOCUMENTS

| | | |
|---|---|---|
| EP | 1130018 A1 | 9/2001 |
| EP | 1634872 A1 | 3/2006 |
| EP | 1829875 A1 | 9/2007 |
| WO | 9616063 A1 | 5/1996 |
| WO | 9846618 A1 | 10/1998 |
| WO | 9959409 A1 | 11/1999 |
| WO | 2006021462 A1 | 3/2006 |
| WO | 2006027221 A1 | 3/2006 |

OTHER PUBLICATIONS

Chih-Cheng Chien et al., "Sigma antagonists potentiate opioid analgesia in rats", Neuroscience Letters, vol. 190, No. 2, 1995, pp. 137-139.
International Search Report for PCT/EP2009/054974, dated Jun. 17, 2009.
Chien et al., "Selective Antagonism of Opioid Analgesia by a Sigma System", J. Pharmacol. Exp. Ther.; 1994; 271; pp. 1583-1590.
Mei et al., "Receptor Modulation of Opioid Analgesia in the Mouse", J. Pharmacol Exp. Ther.; 2002; 300(4); pp. 1070-1074.
Carlsson et al., "Interaction of pentobarbital and morphine in the tail-flick test performed on rats: synergism at the spinal and antagonism at the supraspinal level", NeuroSci. Lett.; 1986; 71; pp. 356-360.
Janicki et al., "Detection of Antagonist Activity for Narcotic Analgesics in Mouse Hot-Plate Test", Pharmacol. Biochem. Behavior, 1979; 10(4); pp. 623-626.
Jianjing Cao, et al "Dual Probes for the Dopamine Transporter and sigmal Receptors: Novel Piperazinyl Alkyl-bis (4-fluorophenyl)amine Analogues as Potential Cocaine-Abuse Therapeutic Agents", J. Med. Chem, No. 13, Mar. 20, 1946, pp. 2589-2598.

(Continued)

Primary Examiner — Sreeni Padmanabhan
Assistant Examiner — Sahar Javanmard
(74) Attorney, Agent, or Firm — Hoffmann & Baron LLP (57) ABSTRACT

The invention relates to the use of a group of sigma receptor ligands of formula (I)

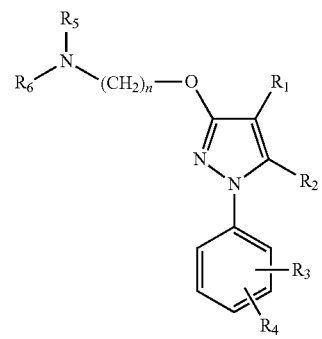

for the potentiation of the analgesic effect of opioids and opiates and at the same time for decreasing the dependency induced by them.

19 Claims, 7 Drawing Sheets

(56) References Cited

OTHER PUBLICATIONS

Nomura Mutsuko et al: "Studies on drug dependence (Rept. 322): Attenuation of morphine- and psychostimulants-induced place preference by sigmal receptor agonist SA4503", Japanese Journal of Pharmacology, The Japanese Pharmacological Society, Kyoto, JP, vol. 79, No. suppl. 1, Jan. 1, 1999, p. 224P.

Sari Izenwasser et al: "Characterization of kappa-opioid receptor binding in human insular cortex", Life Sciences, Pergamon Press, Oxford, GB, vol. 65, No. 9, Jul. 23, 1999, pp. 857-862.

Osipova, N.A., "Tramadol (Tramal) in the Treatment of Acute and Chronic Pain Syndromes," Russky Meditsinsky Zhurnal (Russian Medicinal Journal), Feb. 25, 2003, No. 4, Sections: Pulmonology: Selected Lectures for Family Physicians (Retrieved from the Internet: URL<rmj.ru/number_36.htm).

D.G. Grahame-Smith et al. Oxford textbook on clinical pharmacology and drug therapy M., "Meditsina", 2000, pp. 658-661, Chapter "Narcotic analgesics".

Drug encyclopedia M., RLS, 2001, pp. 572-573, articles "Morphine", "Morphine Sulfate".

Consilium MedSigma-receptors: new potentials of the treatment of depressions. Consilium Medicumicum 2012, vol. 14, No. 2 (found in the Internet: URL<new.consiliummedicum.com/magazines/cm/medicum/article/21505, paragraphs 4-8.

Pirim, A et al.: "Addiction of ketamine infusion to patient controlled analgesia with intravenous morphine after abdominal hysterectomy" Agri Jan. 2006; 18(I):52-8 Abstract.

** P < 0.01, vs corresponding Saline group (Dunnet test)

FIGURE 9

★ P < 0.05, ★★ P < 0.01, vs Preconditioning (Student-t test)

FIGURE 10

1-ARYL-3-AMINOALKOXY PYRAZOLES AS SIGMA LIGANDS ENHANCING ANALGESIC EFFECT OF OPIOIDS AND ATTENUATING THE DEPENDENCY THEREOF

CROSS-REFERENCE TO RELATED APPLICATIONS

This application is the National Stage of International Application No. PCT/EP2009/054974, filed Apr. 24, 2009, which claims the benefit of European Application No. EP08380122.5, filed Apr. 25, 2008, the contents of which are incorporated by reference herein.

FIELD OF THE INVENTION

The present invention relates to potentiation of the analgesic effect of opioids and opiates as well as to attenuation of the addiction thereof. More specifically, the present invention relates to the use of a group of sigma receptor ligands for the potentiation of the analgesic effect of opioids and opiates and for decreasing the dependency induced by them at the same time.

BACKGROUND OF THE INVENTION

Opioids and opiates are potent analgesics widely used in clinical practice. Opioid and opiates drugs are classified typically by their binding selectivity in respect of the cellular and differentiated tissue receptors to which specific drug specie binds as a ligand. These receptors include mu (µ), delta (δ), kappa (κ) and the nociceptive receptors.

The well-known narcotic opiates, such as morphine and its analogues, are selective for the opioid mu receptors. Mu receptors mediate analgesia, respiratory depression, and inhibition of gastrointestinal transit. Kappa receptors mediate analgesia and sedation. However, despite their good activity as analgesics, opioids and opiates have the drawback of causing dependence.

Sigma receptors are non-opiaceous type of receptors of great interest in pharmacology due to their role in analgesia related processes. The sigma binding sites have preferential affinity for the dextrorotatory isomers of certain opiate benzomorphans, such as (+)SKF 10047, (+)cyclazocine, and (+)pentazocine and also for some narcoleptics such as haloperidol. The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

It has been reported that some sigma ligands in combination with opioids or opiates are capable of modulating the analgesic effect thereof. It is known, for example, that haloperidol potentiates the activity of different opioids and opiates such as morphine, DADL or bremazocine [Chichenkov, O. N. et al: Effect of haloperidol on the analgesic activity of intracisternally and intrathecally injected opiate agonists, *Farmakologiya i Toksikologiya* (Moscow) (1985), 48(4), 58-61]. Chien C. et al also referred the synergistic effect of the combination of haloperidol and morphine [Selective antagonism of opioid analgesia by a sigma system, *J Pharmacol Exp Ther* (1994), 271, 1583-1590 and Sigma antagonists potentiate opioid analgesia in rats, *Neurosci Lett* (1995), 190, 137-139] and Marazzo A. et al taught the capacity of the sigma ligand (+)-MR200 to modulate κ-opioid receptor mediated analgesia. Mei J. et al confirmed the importance of sigma-1 receptors as a modulatory system on the analgesic activity of opioid drugs [Sigma1 receptor modulation of opioid analgesia in the mouse, *J Pharmacol Exp Ther* (2002), 300(3), 1070-1074]. Notwithstanding, in all of this cases the problem of dependence induced by opioids and opiates remain to be present.

One of the pharmacological approaches to solve the problem of opioid and opiate dependency has been the co-administration of opioids or opiates and sigma ligands. For instance, sigma-1 receptor agonist SA4503 has been shown to have a modulatory effect on addiction to morphine [Nomura, M. et al: Studies on drug dependence (Rept. 322): Attenuation of morphine- and psychostimulants-induced place preference by sigma1 receptor agonist SA4503, 72nd Annual Meeting of the Japanese Pharmacological Society (Sapporo, Japan-March 1999)]. Also, sigma-1 agonist DHEA has shown some capacity to attenuate the development of morphine dependence [Noda, Y. et al: A neuroactive steroid, dehydroepiandrosterone sulfate, attenuates the development of morphine dependence: an association with sigma1 receptors, $31^{st}$ Annual Meeting of the Society of Neuroscience (San Diego-November 2001)]. EP1130018 teaches the use of sigma ligands for the treatment of drug addiction to morphine, cocaine and methamphetamine. However, none of these approaches show an enhancement of the analgesic effect of morphine.

Therefore, it is desirable to find sigma ligands capable of synergistically potentiate the analgesic effect of opioids or opiates while attenuating at the same time the dependency thereof.

SUMMARY OF THE INVENTION

The inventors of the present invention have surprisingly found that some specific sigma ligands show the capacity to potentiate synergistically the analgesic effects of opioids or opiates while decreasing at the same time the dependency induced by them.

One objective of the present invention relates to a combination of at least one sigma ligand and at least an opioid or opiate compound wherein the sigma ligand has the general formula (I):

wherein
R$_1$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_8$, —$C(O)OR_8$, —$C(O)NR_8R_9$—$C=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, or halogen;

$R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, or halogen;

$R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C=NR_8$, —$CN$, —$OR_8$, —$OC(O)R_8$, —$S(O)_t$—$R_8$, —$NR_8R_9$, —$NR_8C(O)R_9$, —$NO2$, —$N=CR_8R_9$, or halogen, or together they form a fused ring system;

$R_5$ and $R_6$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, or halogen, or together form, with the nitrogen atom to which they are attached, a substituted or unsubstituted heterocyclyl group;

n is selected from 1, 2, 3, 4, 5, 6, 7 or 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

or a pharmaceutically acceptable salt, isomer, prodrug or solvate thereof.

Another objective of this invention refers to the simultaneous, separate or sequential administration of a combination as defined above to potentiate the analgesic effect of an opioid or opiate and/or decrease its dependency.

DETAILED DESCRIPTION OF THE INVENTION

The compounds of formula (I) can be prepared as disclosed in our previous application WO2006021462.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are preferred particularly, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate.

Any compound that is a prodrug of a compound of formula I is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

In a preferred embodiment, $R_1$ in compounds of formula I is selected from H, —$COR_8$, or substituted or unsubstituted alkyl. More preferably, $R_1$ is elected from H methyl of acetyl. A more preferred embodiment is when $R_1$ is H.

In another preferred embodiment, $R_2$ represents H or alkyl, more preferably methyl.

In yet another preferred embodiment of the invention, $R_3$ and $R_4$ are situated in the meta and para positions of the phenyl group, and preferably, they are selected independently from halogen or substituted or unsubstituted alkyl.

In an especially preferred embodiment of the invention, both $R_3$ and $R_4$ together with the phenyl group form a fused ring system, more preferably, a naphthyl ring system.

Also, embodiments where n is selected from 2, 3, 4 are preferred in the context of the present invention.

Finally, in another embodiment it is preferred that $R_5$ and $R_6$ together form a morpholine-4-yl group.

In preferred variants of the invention, it encompasses the combination of at least one opioid or opiate with at least one compound of formula I selected from:

[1] 4-{2-(1-(3,4-dichlorophenyl)-5-methyl-1H pyrazol-3-yloxy)ethyl}morpholine

[2] 2-[1-(3,4-Dichlorophenyl)-5-methyl-1H-pyrazol-3-yloxy]-N,N-diethylethanamine

[3] 1-(3,4-Dichlorophenyl)-5-methyl-3-[2-(pyrrolidin-1-yl)ethoxy]-1H-pyrazole

[4] 1-(3,4-Dichlorophenyl)-5-methyl-3-[3-(pyrrolidin-1-yl)propoxy]-1H-pyrazole

[5] 1-{2-[1-(3,4-Dichlorophenyl)-5-methyl-1H-pyrazol-3-yloxy]ethyl}piperidine

[6] 1-{2-[1-(3,4-dichlorophenyl)-5-methyl-1H-pyrazol-3-yloxy]ethyl}-1H-imidazole

[7] 3-{1-[2-(1-(3,4-Dichlorophenyl)-5-methyl-1H-pyrazol-3-yloxy)ethyl]piperidin-4-yl}-3H-imidazo[4,5-b]pyridine

[8] 1-{2-[1-(3,4-Dichlorophenyl)-5-methyl-1H-pyrazol-3-yloxy]ethyl}-4-methylpiperazine

[9] Ethyl 4-{2-[1-(3,4-dichlorophenyl)-5-methyl-1H-pyrazol-3-yloxy]ethyl}piperazine carboxylate

[10] 1-(4-(2-(1-(3,4-dichlorophenyl)-5-methyl-1H-pyrazol-3-yloxy)ethyl)piperazin-1-yl)ethanone

[11] 4-{2-[1-(4-Methoxyphenyl)-5-methyl-1H-pyrazol-3-yloxy]ethyl}morpholine

[12] 1-(4-Methoxyphenyl)-5-methyl-3-[2-(pyrrolidin-1-yl)ethoxy]-1H-pyrazole

[13] 1-(4-Methoxyphenyl)-5-methyl-3-[3-(pyrrolidin-1-yl)propoxy]-1H-pyrazole

[14] 1-[2-(1-(4-Methoxyphenyl)-5-methyl-1H-pyrazol-3-yloxy)ethyl]piperidine

[15] 1-{2-[1-(4-Methoxyphenyl)-5-methyl-1H-pyrazol-3-yloxy]ethyl}-1H-imidazole

[16] 4-{2-[1-(3,4-Dichlorophenyl)-5-phenyl-1H-pyrazol-3-yloxy]ethyl}morpholine

[17] 1-(3,4-Dichlorophenyl)-5-phenyl-3-[2-(pyrrolidin-1-yl)ethoxy]-1H-pyrazole

[18] 1-(3,4-Dichlorophenyl)-5-phenyl-3-[3-(pyrrolidin-1-yl)propoxy]-1H-pyrazole

[19] 1-{2-[1-(3,4-Dichlorophenyl)-5-phenyl-1H-pyrazol-3-yloxy]ethyl}piperidine

[20] 1-{2-[1-(3,4-Dichlorophenyl)-5-phenyl-1H-pyrazol-3-yloxy]ethyl}-1H-imidazole

[21] 2-{2-[1-(3,4-dichlorophenyl)-5-phenyl-1H-pyrazol-3-yloxy]ethyl}-1,2,3,4-tetrahydroisoquinoline

[22] 4-{4-[1-(3,4-Dichlorophenyl)-5-methyl-1H-pyrazol-3-yloxy]butyl}morpholine

[23] 1-(3,4-Dichlorophenyl)-5-methyl-3-[4-(pyrrolidin-1-yl)butoxy]-1H-pyrazole

[24] 1-{4-[1-(3,4-Dichlorophenyl)-5-methyl-1H-pyrazol-3-yloxy]butyl}piperidine

[25] 1-{4-[1-(3,4-Dichlorophenyl)-5-methyl-1H-pyrazol-3-yloxy]butyl}-4-methylpiperazine

[26] 1-{4-[1-(3,4-Dichlorophenyl)-5-methyl-1H-pyrazol-3-yloxy]butyl}-1H-imidazole

[27] 4-[1-(3,4-Dichlorophenyl)-5-methyl-1H-pyrazol-3-yloxy]-N,N-diethylbutan-1-amine
[28] 1-{4-[1-(3,4-dichlorophenyl)-5-methyl-1H-pyrazol-3-yloxy]butyl}-4-phenylpiperidine
[29] 1-{4-[1-(3,4-dichlorophenyl)-5-methyl-1H-pyrazol-3-yloxy]butyl}-6,7-dihydro-1H-indol-4(5H)-one
[30] 2-{4-[1-(3,4-dichlorophenyl)-5-methyl-1H-pyrazol-3-yloxy]butyl}-1,2,3,4-tetrahydroisoquinoline
[31] 4-{2-[1-(3,4-dichlorophenyl)-5-isopropyl-1H-pyrazol-3-yloxy]ethyl}morpholine
[32] 2-[1-(3,4-Dichlorophenyl)-5-isopropyl-1H-pyrazol-3-yloxy]-N,N-diethylethanamine
[33] 1-(3,4-Dichlorophenyl)-5-isopropyl-3-[2-(pyrrolidin-1-yl)ethoxy]-1H-pyrazole
[34] 1-(3,4-Dichlorophenyl)-5-isopropyl-3-[3-(pyrrolidin-1-yl)propoxy]-1H-pyrazole
[35] 1-{2-[1-(3,4-Dichlorophenyl)-5-isopropyl-1H-pyrazol-3-yloxy]ethyl}piperidine
[36] 2-{2-[1-(3,4-dichlorophenyl)-5-isopropyl-1H-pyrazol-3-yloxy]ethyl}-1,2,3,4-tetrahydroisoquinoline
[37] 4-{2-[1-(3,4-dichlorophenyl)-1H-pyrazol-3-yloxy]ethyl}morpholine
[38] 2-[1-(3,4-dichlorophenyl)-1H-pyrazol-3-yloxy]N,N-diethylethanamine
[39] 1-(3,4-dichlorophenyl)-3-[2-(pyrrolidin-1-yl)ethoxy]-1H-pyrazole
[40] 1-{2-[1-(3,4-dichlorophenyl)-1H-pyrazol-3-yloxy]ethyl}piperidine
[41] 1-(3,4-dichlorophenyl)-3-[3-(pyrrolidin-1-yl)propoxy]-1H-pyrazole
[42] 1-{2-[1-(3,4-Dichlorophenyl)-5-methyl-1H-pyrazol-3-yloxy]ethyl}piperazine
[43] 1-{2-[1-(3,4-Dichlorophenyl)-5-methyl-1H-pyrazol-3-yloxy]ethyl}pyrrolidin-3-amine
[44] 4-{2-[1-(3,4-Dichlorophenyl)-4,5-dimethyl-1H-pyrazol-3-yloxy]ethyl}morpholine
[45] 4-{2-[1-(3,4-Dichlorophenyl)-4,5-dimethyl-1H-pyrazol-3-yloxy]ethyl}morpholine
[46] 2-[1-(3,4-Dichlorophenyl)-4,5-dimethyl-1H-pyrazol-3-yloxy]-N,N-diethylethanamine
[47] 1-(3,4-Dichlorophenyl)-4,5-dimethyl-3-[2-(pyrrolidin-1-yl)ethoxy]-1H-pyrazole
[48] 1-(3,4-Dichlorophenyl)-4,5-dimethyl-3-[3-(pyrrolidin-1-yl)propoxy]-1H-pyrazole
[49] 1-{2-[1-(3,4-Dichlorophenyl)-4,5-dimethyl-1H-pyrazol-3-yloxy]ethyl}piperidine
[50] 4-{4-[1-(3,4-dichlorophenyl)-1H-pyrazol-3-yloxy]butyl}morpholine
[51] (2S,6R)-4-{4-[1-(3,4-dichlorophenyl)-1H-pyrazol-3-yloxy]butyl}-2,6-dimethylmorpholine
[52] 1-{4-[1-(3,4-Dichlorophenyl)-1H-pyrazol-3-yloxy]butyl}piperidine
[53] 1-(3,4-Dichlorophenyl)-3-[4-(pyrrolidin-1-yl)butoxy]-1H-pyrazole
[55] 4-[1-(3,4-dichlorophenyl)-1H-pyrazol-3-yloxy]-N,N-diethylbutan-1-amine
[56] N-benzyl-4-[1-(3,4-dichlorophenyl)-1H-pyrazol-3-yloxy]-N-methylbutan-1-amine
[57] 4-[1-(3,4-dichlorophenyl)-1H-pyrazol-3-yloxy]-N-(2-methoxyethyl)-N-methylbutan-1-amine
[58] 4-{4-[1-(3,4-dichlorophenyl)-1H-pyrazol-3-yloxy]butyl}thiomorpholine
[59] 1-[1-(3,4-Dichlorophenyl)-5-methyl-3-(2-morpholinoethoxy)-1H-pyrazol-4-yl]ethanone
[60] 1-{1-(3,4-dichlorophenyl)-5-methyl-3-[2-(pyrrolidin-1-yl)ethoxy]-1H-pyrazol-4-yl}ethanone
[61] 1-{1-(3,4-dichlorophenyl)-5-methyl-3-[2-(piperidin-1-yl)ethoxy]-1H-pyrazol-4-yl}ethanone
[62] 1-{1-(3,4-dichlorophenyl)-3-[2-(diethylamino)ethoxy]-5-methyl-1H-pyrazol-4-yl}ethanone
[63] 4-{2-[5-Methyl-1-(naphthalen-2-yl)-1H-pyrazol-3-yloxy]ethyl}morpholine
[64] N,N-Diethyl-2-[5-methyl-1-(naphthalen-2-yl)-1H-pyrazol-3-yloxy]ethanamine
[65] 1-{2-[5-Methyl-1-(naphthalen-2-yl)-1H-pyrazol-3-yloxy]ethyl}piperidine
[66] 5-Methyl-1-(naphthalen-2-yl)-3-[2-(pyrrolidin-1-yl)ethoxy]-1H-pyrazole or their pharmaceutically acceptable salts, solvates or a prodrug thereof.

Opioids and opiates are compounds that bind to opioid receptors. Compounds that bind to the opioid receptor within the scope of the present invention include natural opiates, such as morphine, codeine and thebaine; semi-synthetic opiates, derived from the natural opioids, such as hydromorphone, hydrocodone, oxycodone, oxymorphone, desomorphine, diacetylmorphine, nicomorphine, dipropanoylmorphine, benzylmorphine and ethylmorphine; fully synthetic opioids, such as fentanyl, pethidine, methadone, tramadol and propoxyphene; and endogenous opioid peptides, produced naturally in the body, such as endorphins, enkephalins, dynorphins, and endomorphins and their analogues. Preferably, the opioid receptor ligand utilized according to this invention is morphine or its analogues.

The term "analogue" in the context of this invention refers to any entity structurally derived or homologous to a compound that binds to an opioid receptor and ellicit an analgesic effect. Examples of analogues according to this definition, include the morphine analogues disclosed, for instance, in EP0975648 or EP0793364.

The preferred combination of the invention comprises the combination of 4-{2-[5-Methyl-1-(naphthalen-2-yl)-1H-pyrazol-3-yloxy]ethyl}morpholine and morphine.

The combination of the invention may be formulated for its simultaneous separate or sequential administration, with at least a pharmaceutically acceptable carrier, additive, adjuvant or vehicle. This has the implication that the combination of the two active compounds may be administered:

a) As a combination that is being part of the same medicament formulation, the two active compounds being then administered always simultaneously.

b) As a combination of two units, each with one of the active substances giving rise to the possibility of simultaneous, sequential or separate administration. In a particular embodiment, the sigma ligand is independently administered from the opioid or opiate (i.e in two units) but at the same time. In another particular embodiment, the sigma ligand is administered first, and then the opioid or opiate is separately or sequentially administered. In yet another particular embodiment, the opioid or opiate is administered first, and then the sigma ligand is administered, separately or sequentially, as defined.

Each of these particular and different ways of administration produce the desired effect: to potentiate synergistically the opioid or opiate analgesia and/or attenuate its dependence.

The auxiliary materials or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical combination in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are tablets, pills, chewing gums, capsules, granules, drops or syrups.

Suitable preparations for parenteral applications are solutions, suspensions, reconstitutable dry preparations or sprays.

The combination of the invention may be formulated as deposits in dissolved form or in patches, for percutaneous application.

Skin applications include ointments, gels, creams, lotions, suspensions or emulsions.

The preferred form of rectal application is by means of suppositories.

The combination of at least one opioid or opiate and at least one compound of general formula I are suited for use in potentiating the analgesic effect of opioids or opiates and/or for decreasing their dependency. These combinations could be administered simultaneously, separately or sequentially.

The combination of the invention shows both the effect of potentiating the analgesia produced by opioids or opiates and for decreasing their dependency but could be used; in any case, to achieve solely one of these objectives.

For example, for the co-administration of a compound of formula (I) and an opioid or opiate could be directed only to maximize the opioid or opiate analgesic effect. Under this scenario, it will be possible to attain the added benefit of maintaining the same analgesic level while reducing the opioid or opiate dosage.

In another embodiment, the administration may be intended just for the attenuation of the dependency or addiction induced by opioids or opiates.

In a preferred embodiment, the invention comprises the use of a combination se defined herein for both potentiating the analgesic effect of opioids or opiates and decreasing at the same time the dependency induced by them.

The dosage regime that must be administered to the patient depends on the patient's weight, the type of application, the condition and severity of the disease. A preferred dosage regime of comprises an administration of a compound of formula (I) within a range of 0.5 to 100 mg/kg and of the opioid or opiate from 0.15 to 15 mg/kg and it is administered daily in one or several doses.

Another object of the invention is based on the discovery that sigma ligands are capable at the same time of synergistically enhancing the analgesic effect of opioids and opiates and decreasing the dependence induced by them. This aspect of the invention comprises a combination of at least one sigma ligand and at least an opioid or opiate compound. The combination is then administered in a simultaneous, separate or sequential manner to potentiate the analgesic effect of the opioid or opiate and decrease its dependency.

In another embodiment of the present invention, the opiate used is preferably morphine or analogues thereof.

The following examples will serve to illustrate the invention.

Example 1

Synergistic Effect of Compound 63 in Analgesia Mediated by Morphine a) Modulation of Morphine Analgesia in the Tail Flick Test The analgesia induced by the combination of compound 63, a sigma-1 ligand, and morphine was assessed by the tail flick test following the method described by Carlsson et al [Neurosci Lett. 1986 Nov. 21; 71(3):356-60] in CD-1 wild type (WT) mice as well as in sigma-1 deficient mice (KO).

Figure 1:
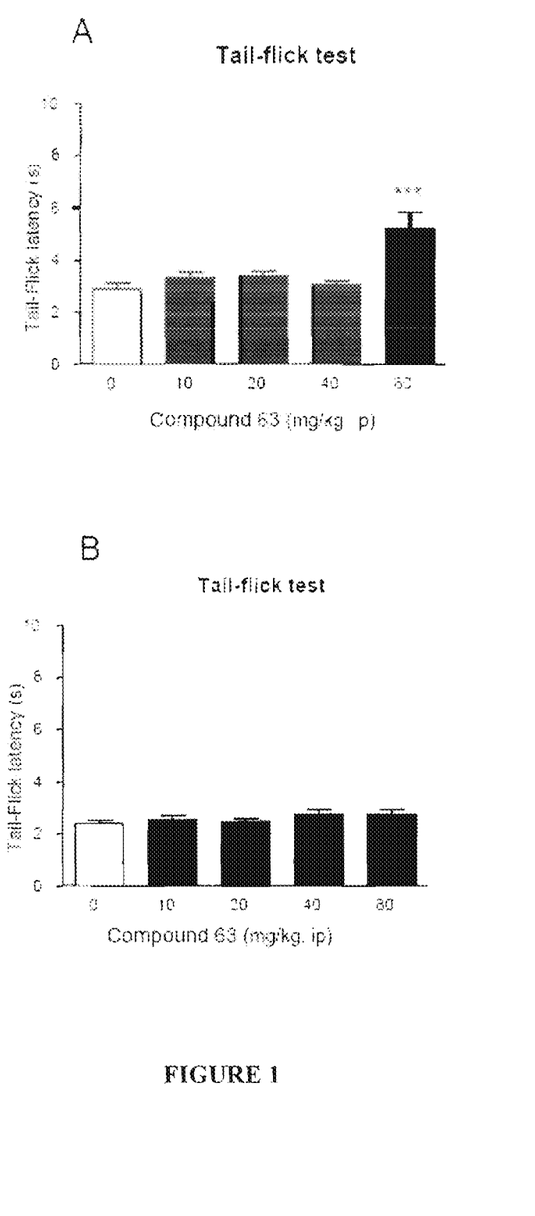
FIG. 1: Dose-response effects of acute administration of compound 63 (10, 20, 40 and 80 mg/kg, i.p.) in the tail-flick test in male CD-1 WT mice (A) and in CD-1 σ1R-KO mice (B). Compounds were injected 30 min before the test. Data, obtained from 12 (A) or 10 (B) animals per group, are presented as the mean±SEM of the tail-flick latency (s). ***$p<0.001$ vs. vehicle (HPMC 0.5%) treated group (Newman-Keuls Multiple comparison Test post-ANOVA).

First, the efficacy of compound 63 alone was evaluated in WT as well as KO mice by its administration at different doses (10, 20, 40 and 80 mg/kg, i.p.). Compound 63 had no significant effect on response latency except for the highest dose tested. As expected, this effect was even no present for KO mice (see FIG. 1).

Figure 2:
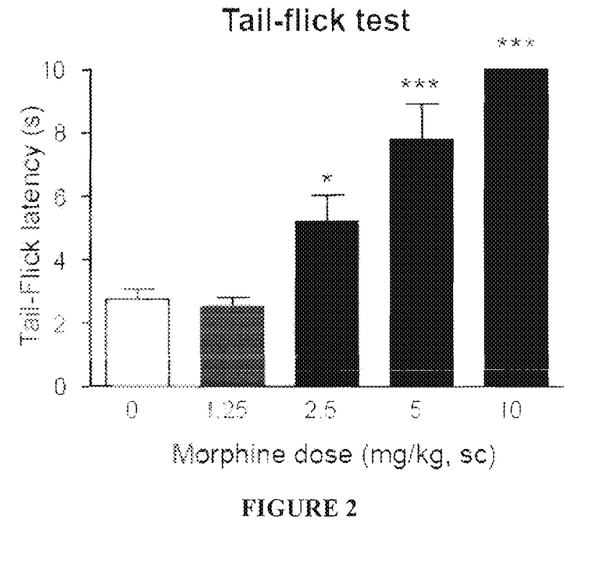
FIG. 2: Dose-response effects of acute administration of morphine (1.25, 2.5, 5 and 10 mg/kg, sc) in the tail-flick test in male CD-1 WT mice. Compounds were injected 30 min before the test. Data, obtained from 8 animals per group, are presented as the mean±SEM of the tail-flick latency (s). *$p<0.05$, ***$p<0.001$ vs. vehicle (saline) treated group (Newman-Keuls Multiple comparison Test post-ANOVA).
Figure 3:
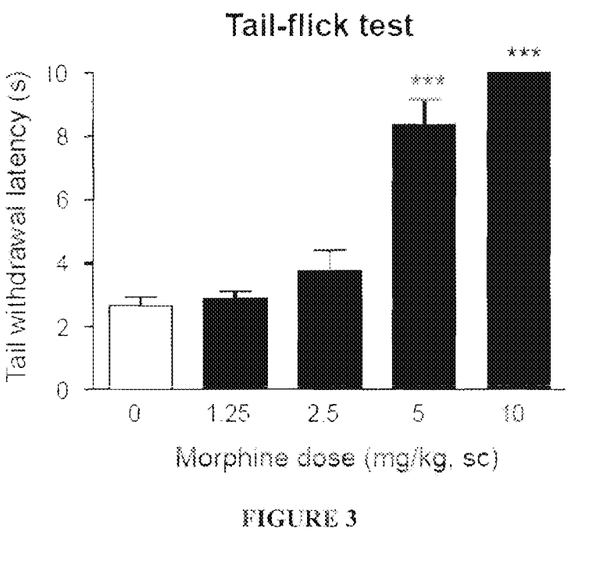
FIG. 3: Dose-response effects of acute administration of morphine (1.25, 2.5, 5 and 10 mg/kg, sc) in the tail-flick test in male CD-1 σ1R-KO mice. Compounds were injected 30 min before the test. Data, obtained from 10 to 11 animals per group, are presented as the mean±SEM of the tail-flick latency (s). ***$p<0.001$ vs. vehicle (saline) treated group (Newman-Keuls Multiple comparison Test post-ANOVA).
Figure 4:
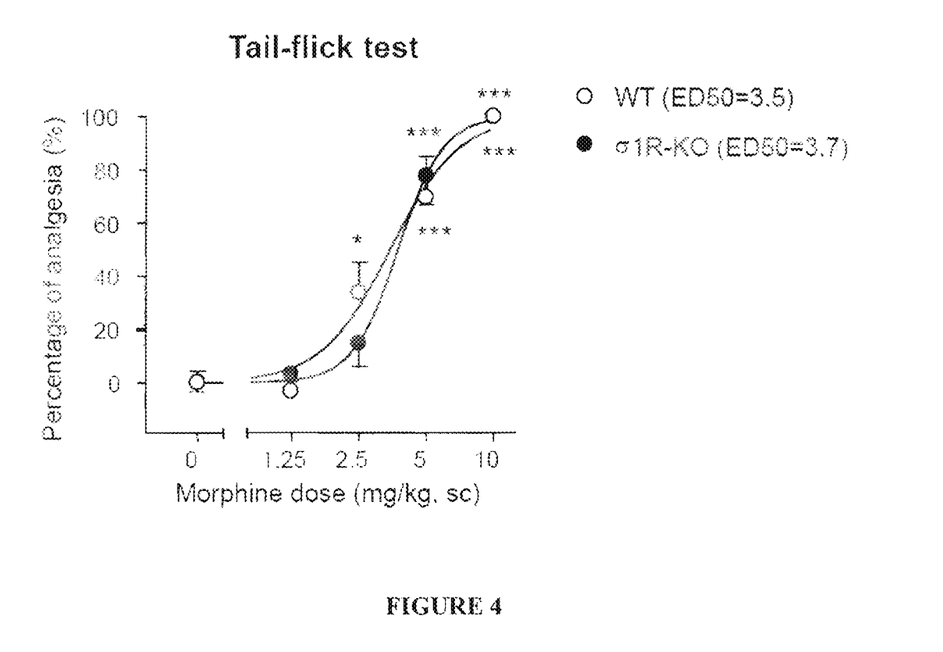
FIG. 4: Sigmoidal dose-response curves of morphine (1.25, 2.5, 5 and 10 mg/kg, sc) in the tail-flick test in male CD-1 WT and σ1R-KO mice. Compounds were injected 30 min before the test. Data, obtained from 8 to 11 animals per group, are presented as the mean±SEM percentages of analgesia (%). Insert: Tail-Flick latency of both, WT and σ1R-KO, vehicle treated groups. *$p<0.05$, ***$p<0.001$ vs. corresponding vehicle group (saline) (Newman-Keuls Multiple comparison Test post-ANOVA).

In contrast morphine produced a clear dose-dependent analgesic effect either in WT and KO mice with similar efficacy and potency (ED 50 3.5 and 3.7 mg/kg for WT and KO, respectively) indicating that KO mice perceive normally the morphine analgesia in these conditions of tail flick assay (see FIGS. 2, 3 and 4).

Figure 5:
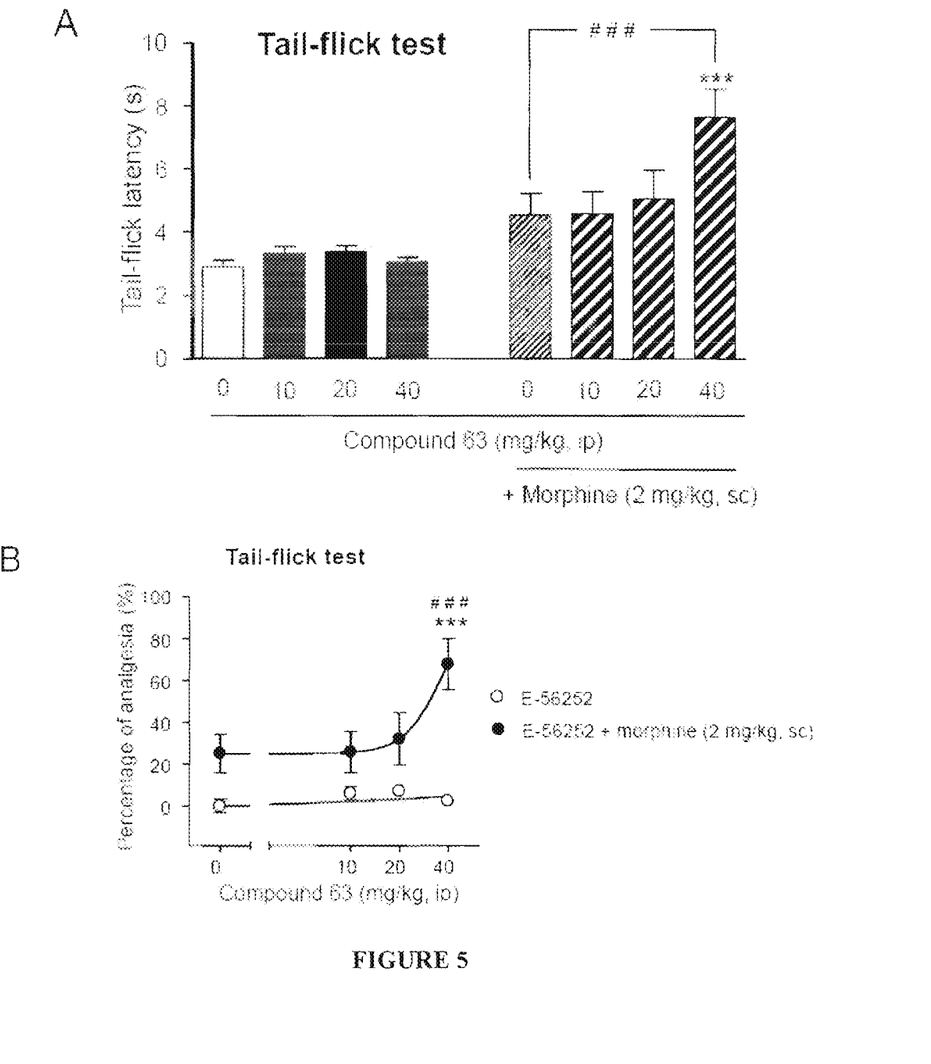
FIG. 5: A) Potentiation of the antinociceptive actions of morphine (2 mg/kg, sc) by compound 63 (10, 20, 40 mg/kg, ip) in the tail-flick test in male CD-1 WT mice. Compounds were injected 30 min before the test. Data, obtained from 11 to 12 animals per group, are presented as the mean±SEM of the tail-flick latency (s). ***$p<0.001$ vs. vehicle treated group; ###$p<0.001$ vs. morphine (2 mg/kg) group (Newman-Keuls Multiple comparison Test post-ANOVA). B) Sigmoidal dose-response curves representation.

Next, the analgesia produced by the combination of compound 63 and morphine was evaluated in WT mice. FIG. 5 shows the potentiation of the antinociceptive action of morphine (2 mg/kg, s.c.) by compound 63 represented by the tail flick latency (A) and by the percentage of analgesia (B).

Figure 6:
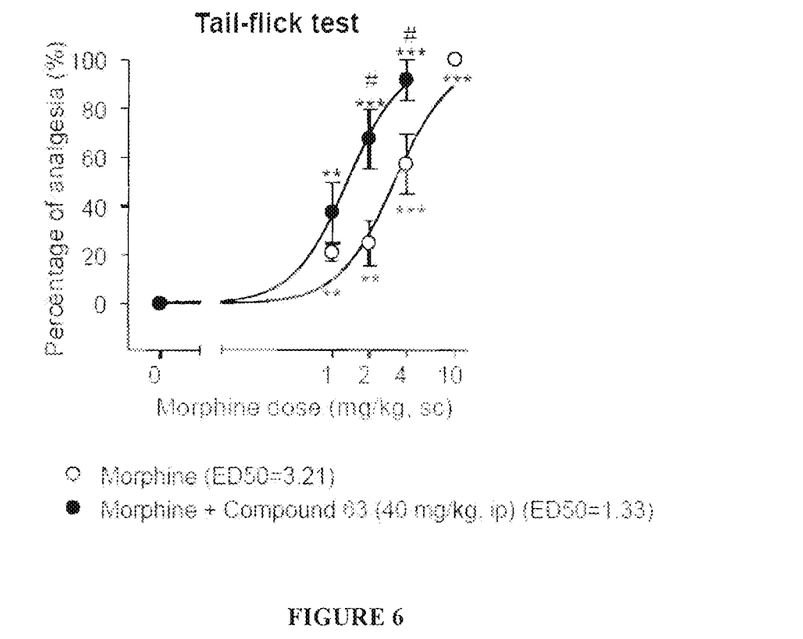
FIG. 6: Sigmoidal dose-response curves of morphine (1, 2, 4, and 10 mg/kg, sc) and combination of compound 63 (40 mg/kg, ip) with morphine (1, 2 and 4 mg/kg, sc) in the tail-flick test in male CD-1 WT mice. Compounds were injected 30 min before the test. Data, obtained from 10 to 11 animals per group, are presented as the mean±SEM percentages of analgesia (%). $p<0.01$; *$p<0.001$ vs. corresponding vehicle treated group (Newman-Keuls Multiple comparison Test post-ANOVA).; #$p<0.05$ vs. corresponding group treated with morphine (2 and 4 mg/kg) (Unpaired t-test).

As shown in FIG. 6, the sigmoidal dose response curves in CD1 WT mice of the combination of morphine (1, 2 and 4 mg/kg, s.c.) with compound 63 (40 mg/kg, i.p.) when compared to morphine alone (1, 2, 4 and 10 mg/kg, s.c.) shows a significant increase in the percentage of analgesia of the combination and a significant decrease in the ED50 of the combination (ED50=1.33) vs morphine alone (ED50=3.21). The combination of morphine with 40 mg/kg of compound 63 increases the analgesia potency of morphine alone by a factor of 2.4.

Figure 7:
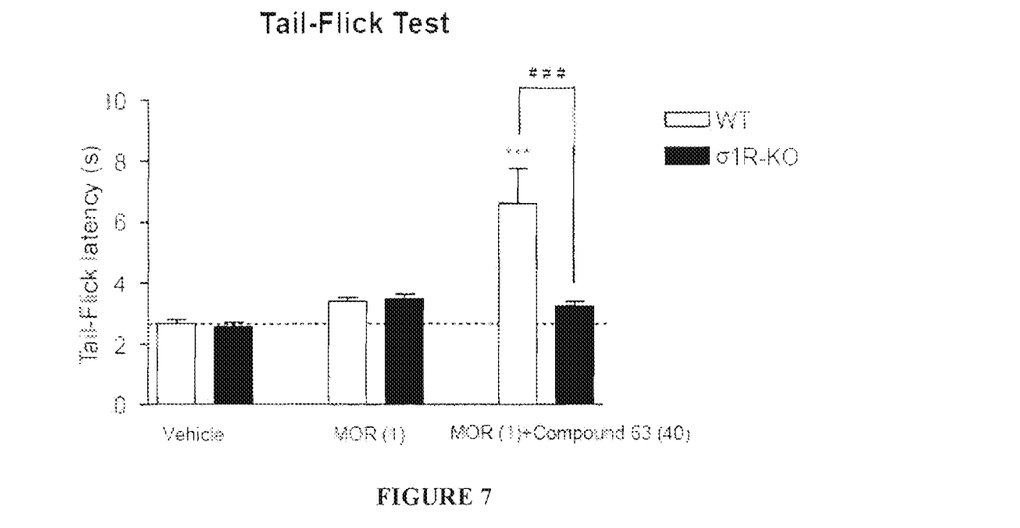
FIG. 7: Antinociceptive effect of morphine (MOR) and the combination of morphine+compound 63 in the tail-flick test in WT and σ1R-KO male CD-1 mice. Compounds were injected intraperitoneally 30 min before the test. Dose of drugs are expressed in mg/kg (brackets in the graph). Data, obtained from 6 to 14 animals per group, are presented as the mean±SEM of the tail-flick latency (s). ***$p<0.001$ vs. vehicle treated WT group; ###$p<0.001$ vs. MOR+compound 63 treated WT group. (Newman-Keuls Multiple comparison Test post-ANOVA).

Groups of mice received morphine alone (1 mg/kg) and in combination with compound 63 (40 mg/kg) and it was found only 10% of analgesia with morphine alone (no significant) and 55% of analgesia with the combination. This synergistic effect is, however, abolished when the combination is administered to sigma-1 KO mice as shown in FIG. 7.

b) Modulation of Morphine Analgesia in the Hot Plate Test

In order to further study the effect of compound 63 on morphine analgesia, experiments were performed in the hot-plate (supraspinally integrated responses) as described by Janicki et al [Pharmacol Biochem Behave. 1979 April; 10(4):623-6]. The effect of compound 63 on morphine analgesia was examined: groups of mice received morphine alone (2.5 mg/kg) and in combination with compound 63 (40 mg/kg). When the hot-plate test is performed at 50° C., we found a 45% of analgesic activity with morphine alone, and 83% with the morphine and compound 63 combination. When it is performed at 55° C., morphine produced 43% of analgesic activity and the combination 94%. Therefore, compound is able to enhance morphine analgesia also in the hot-plate test.

Example 2

Enhanced Synergistic Effect of Compound 63 and 11 in Analgesia Mediated by Morphine when Compared to Well Known Sigma Ligand BD1063

The analgesic effect of two of the compounds of the invention (compound 63 and compound II) and of BD1063 well known sigma-1 ligand in combination with morphine was evaluated in CD-1 wild type (WT) mice by the tail flick test as under example 1. Compound 63 and 11 and BD1063 where administered in a single dose of 40 mg/kg i.p 30 minutes before the administration of morphine (1 mg/kg s.c.)

Figure 8:
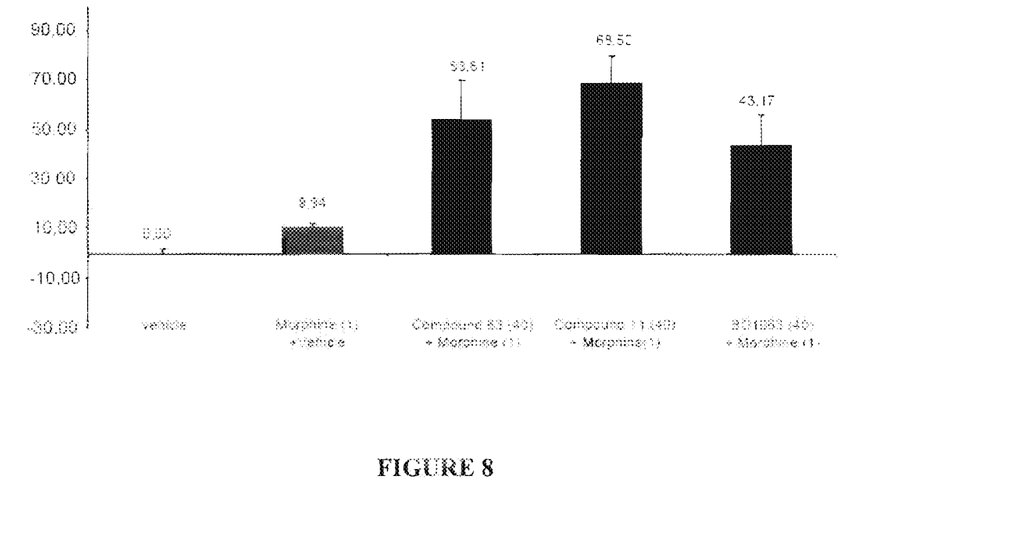
FIG. 8: Enhanced synergistic effect of compound 63 and 11 in analgesia mediated by morphine when compared to well known sigma ligand BD1063.

The results shown in FIG. 8 demonstrate that all combination of sigma ligand with morphine produced an enhancement of the analgesic effect of morphine although this effect was more pronounced in the case of the co administration with the compound 63 and 11 of the present invention.

Example 3

Attenuation of Dependence Induced by Morphine by Co-Administration with Compound 63

The attenuation of the addictive effect of morphine by compound 63 was tested with the place conditioning paradigm model. The place conditioning paradigm is a behavioural model used in mice to evaluate the possible rewarding/aversive properties of a drug. In this paradigm the rewarding effects of the drug are associated with the physical characteristics of an environment, and thus, mice will prefer spend more time in the environment associated with a drug having rewarding properties. This model also allows exploring the aversive effects of a drug, and in this case, the mouse will avoid stay in the compartment associated with the drug having aversive properties.

The purpose was to evaluate the effects induced by the administration compound 63 in the mouse place conditioning paradigm and their capability to modify the rewarding properties of morphine in this paradigm. Two different doses of morphine were tested and compound 63 was administered at a single dose calculated from the data previously obtained in the neuropathic pain model (data not shown).

Male CD-1 mice (Charles River, France) weighing 20-22 gr at the beginning of the experiment were used. Mice were identified by a mark on the tail and housed individually in controlled laboratory conditions with the temperature maintained at $21\pm1°$ C., humidity at $55\pm10\%$, and light controlled cycle (light on at 08:00 h; light off at 20:00 h). All experiments were conducted in a sound attenuated room. The mice were given access to food and water ad libitum except during the behavioural testing. All experimental procedures and animal husbandry were conducted according to standard ethical guidelines (European Community Guidelines on the Care and Use of Laboratory Animals) and approved by the local ethical committee.

The following experimental groups were tested:
Group 1 (n=12): saline+saline
Group 2 (n=14): morphine (1.5 mg/kg s.c.)+saline
Group 3 (n=11): morphine (5 mg/kg s.c.)+saline
Group 4 (n=12): saline+compound 63 (25 mg/kg s.c.)
Group 5 (n=11): morphine (1.5 mg/kg s.c.)+compound 63 (25 mg/kg s.c.)
Group 6 (n=12): morphine (5 mg/kg s.c.)+compound 63 (25 mg/kg s.c.)

The rewarding properties of morphine and the possible rewarding/aversive effect of compound 63 were evaluated by using an apparatus adapted for the conditioning place preference paradigm. The apparatus consists of two main square conditioning compartments separated by a triangular central division. During the preconditioning phase, each mouse was placed in the middle of the central division and had free access to both compartments of the conditioning apparatus for 18 min, with the time spent in each compartment recorded. Treatments were counterbalanced between compartments in order to use an unbiased procedure. For conditioning phase, mice were treated during 6 days with alternate injections of drugs (morphine and/or compound 63) or saline. Saline and compound 63 were administered 30 min before morphine or saline injection. Mice were confined into the corresponding compartment immediately after morphine or saline administration by using guillotine doors matching walls for 20 min. Drugs were administered on days 1, 3 and 5, and saline on days 2, 4 and 6. Control animals received saline every day. The test phase was conducted as in the preconditioning phase, i.e. free access to both compartments for 18 min, and the time spent in each compartment was recorded. A score was calculated for each mouse as the difference between the post-conditioning and pre-conditioning time spent in the drug-paired compartment. Data were expressed as raw time score values (seconds) (FIG. 9) and time spent in the drug-paired compartment during pre-conditioning and test phases (seconds) (FIG. 10). Time score values were compared using one-way ANOVA (between subjects) followed by a Dunnet post-hoc comparison. Values of the time spent for each group of mice in drug-paired compartment during the pre-conditioning and post-conditioning measurements were compared by using a two-tailed Student's paired t-test.

Figure 9:
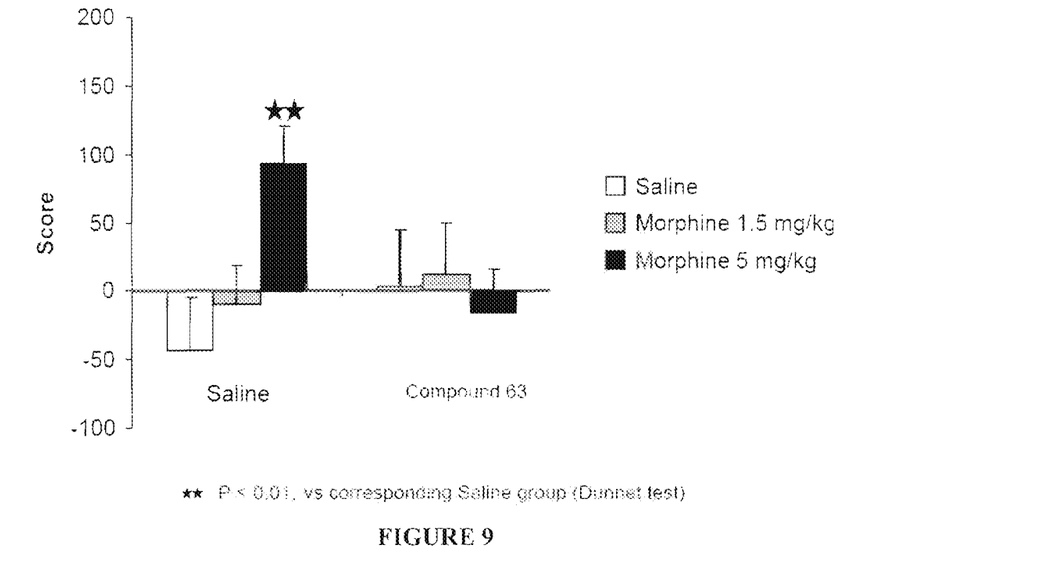
FIG. 9: Effect of compound 63 (25 mg/kg s.c) on the rewarding effects induced by morphine in the place conditioning paradigm (score values).
Figure 10:
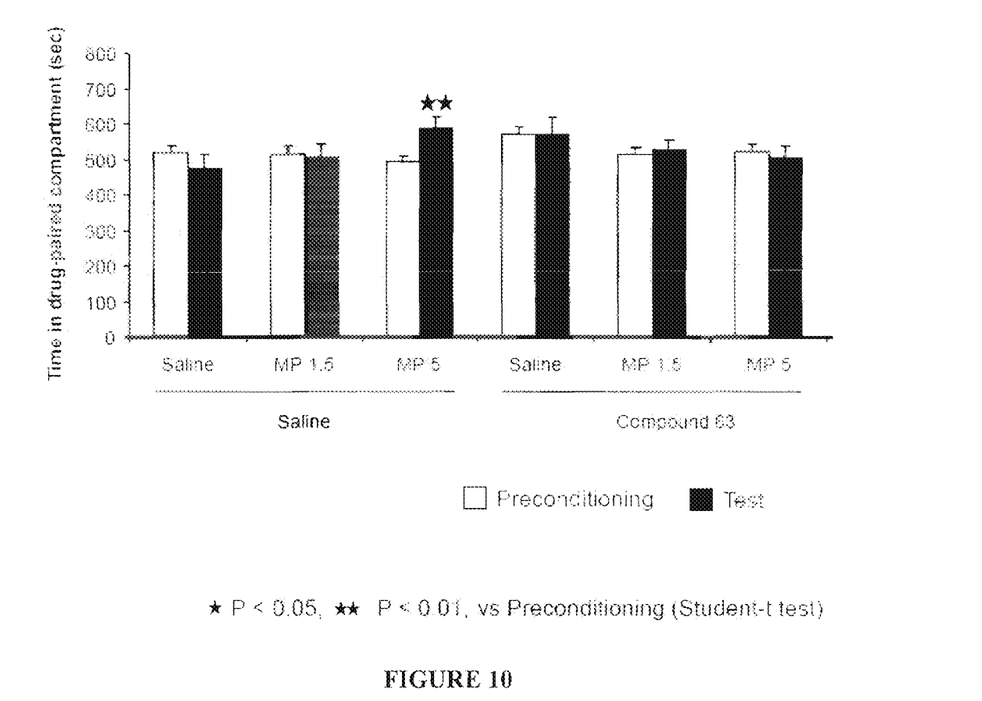
FIG. 10: Effect of compound 63 (25 mg/kg s.c.) on the rewarding effects induced by morphine in the place conditioning paradigm. Time spent in the drug paired compartment during the preconditioning and test phase.

The results as shown in FIGS. 9 and 10 give rise to the following conclusions:

Morphine administered at the dose of 5 mg/kg induced rewarding effects revealed by a conditioned place preference: No effects were observed when morphine was administered at the dose of 1.5 mg/kg. These effective and non-effective doses of morphine were used to evaluate the possible interactions with compound 63.

Compound 63 (25 mg/kg) did not produce any place conditioning effect when administered alone. This result suggests that compound 63 does not produce rewarding or aversive effects when administered at this dose.

Compound 63 (25 mg/kg) attenuated the rewarding effects induced by morphine in the place conditioning paradigm. Thus, compound 63 suppressed the rewarding responses produced by the effective dose of morphine (5 mg/kg) and did not produce any conditioned response when it was associated to the non-effective dose of morphine (1.5 mg/kg).

The invention claimed is:

1. A combination for simultaneous, separate or sequential administration comprising:
a) at least one sigma ligand selected from the group consisting of 4-{2-[1-(4-methoxyphenyl)-5-methyl-1H-pyrazol-3-yloxy]ethyl}morpholine, 4-{2-[5-methyl-1-(naphthalen-2-yl)-1H-pyrazol-3-yloxy]

ethyl}morpholine and pharmaceutically acceptable salts, isomers and solvates thereof; and
  b) at least one opioid or opiate compound selected from the group consisting of morphine, fentanyl and tramadol.

2. The combination of claim 1 wherein the sigma ligand is 4-{2-[1-(4-methoxyphenyl)-5-methyl-1H-pyrazol-3-yloxy]ethyl}morpholine or a pharmaceutically acceptable salt, isomer or solvate thereof.

3. The combination of claim 1 wherein the sigma ligand is 4-{2-[5-methyl-1-(naphthalen-2-yl)-1H-pyrazol-3-yloxy]ethyl}morpholine or a pharmaceutically acceptable salt, isomer or solvate thereof.

4. The combination of claim 1 wherein the opioid or opiate compound is morphine.

5. The combination of claim 1 wherein the opioid or opiate compound is fentanyl.

6. The combination of claim 1 wherein the opioid or opiate compound is tramadol.

7. The combination of claim 1 wherein the combination comprises 4-{2-[1-(4-methoxyphenyl)-5-methyl-1H-pyrazol-3-yloxy]ethyl}morpholine or a pharmaceutically acceptable salt, isomer or solvate thereof and morphine.

8. The combination of claim 1 wherein the combination comprises 4-{2-[1-(4-methoxyphenyl)-5-methyl-1H-pyrazol-3-yloxy]ethyl}morpholine or a pharmaceutically acceptable salt, isomer or solvate thereof and fentanyl.

9. The combination of claim 1 wherein the combination comprises 4-{2-[1-(4-methoxyphenyl)-5-methyl-1H-pyrazol-3-yloxy]ethyl}morpholine or a pharmaceutically acceptable salt, isomer or solvate thereof and tramadol.

10. The combination of claim 1 wherein the combination comprises 4-{2-[5-methyl-1-(naphthalen-2-yl)-1H-pyrazol-3-yloxy]ethyl}morpholine or a pharmaceutically acceptable salt, isomer or solvate thereof and morphine.

11. The combination of claim 1 wherein the combination comprises 4-{2-[5-methyl-1-(naphthalen-2-yl)-1H-pyrazol-3-yloxy]ethyl}morpholine or a pharmaceutically acceptable salt, isomer or solvate thereof and fentanyl.

12. The combination of claim 1 wherein the combination comprises 4-{2-[5-methyl-1-(naphthalen-2-yl)-1H-pyrazol-3-yloxy]ethyl}morpholine or a pharmaceutically acceptable salt, isomer or solvate thereof and tramadol.

13. A method for potentiating the analgesic effect of morphine, fentanyl or tramadol and/or for decreasing the dependency induced thereby, comprising administering to a patient in need thereof, a therapeutically effective amount of a combination as defined in claim 1.

14. The method of claim 13 for potentiating the analgesic effect of morphine, fentanyl or tramadol.

15. The method of claim 13 for decreasing the dependency induced by morphine, fentanyl or tramadol.

16. The method of claim 13, comprising administering to a patient in need thereof, a therapeutically effective amount of a combination as defined in claim 1 simultaneous, separate or sequentially.

17. The method of claim 13, comprising administering to a patient in need thereof, a therapeutically effective amount of a combination of 4-{2-[5-methyl-1-(naphthalen-2-yl)-1H-pyrazol-3-yloxy]ethyl}morpholine or a pharmaceutically acceptable salt, isomer or solvate thereof and morphine.

18. The method of claim 13, comprising administering to a patient in need thereof, a therapeutically effective amount of a combination of 4-{2-[5-methyl-1-(naphthalen-2-yl)-1H-pyrazol-3-yloxy]ethyl}morpholine or a pharmaceutically acceptable salt, isomer or solvate thereof and fentanyl.

19. The method of claim 13, comprising administering to a patient in need thereof, a therapeutically effective amount of a combination of 4-{2-[5-methyl-1-(naphthalen-2-yl)-1H-pyrazol-3-yloxy]ethyl}morpholine or a pharmaceutically acceptable salt, isomer or solvate thereof and tramadol.

* * * * *